United States Patent [19]

Ryder et al.

[11] Patent Number: 4,873,424
[45] Date of Patent: Oct. 10, 1989

[54] WALL PLUG LENS DISINFECTOR

[75] Inventors: Francis E. Ryder, Arab; Rowland W. Kanner, Guntersville; Fred E. Williams, Arab, all of Ala.

[73] Assignee: Ryder International Corporation, Arab, Ala.

[21] Appl. No.: 221,283

[22] Filed: Jul. 19, 1988

[51] Int. Cl.$^4$ ............................................. H05B 3/14
[52] U.S. Cl. ..................................... 219/521; 219/386
[58] Field of Search ............... 219/521, 385, 386, 438, 219/439, 441, 387; 422/199, 292

[56] References Cited

U.S. PATENT DOCUMENTS

| | | | |
|---|---|---|---|
| 4,242,572 | 12/1980 | Thomas | 422/199 |
| 4,307,289 | 12/1981 | Thomas | 219/521 |
| 4,388,521 | 6/1983 | Thomas | 219/521 |
| 4,677,280 | 6/1987 | Kai | 219/521 |

Primary Examiner—Teresa J. Walberg
Attorney, Agent, or Firm—R. A. Giangiorgi

[57] ABSTRACT

An appliance for electrically heated disinfection of contact lenses or similar ojects is provided with a molded plastic housing having a recessed cavity for insertion of a conventional side-by-side horizontal lens storage case containing the lenses immersed in disinfecting liquid, typically saline solution. The cavity has horizontally aligned opposite end openings through the sides of the housing and the openings are located and dimensioned to allow unobstructed sliding passage of the lens case from the cavity so that the lens case will fall by gravitation from the cavity through one of the openings when the housing is rotated 90° to vertically align the openings. The cavity openings thus ensure that the lens case cannot be heated in the appliance in a vertical orientation which could damage the lenses by heated exposure above the level of the disinfecting liquid. The housing further includes a floor wall below the cavity and a cover portion overlying the cavity for preventing vertical access to the lens case and filling the case with saline solution when installed in the cavity. The appliance further includes components for electrically heating the lens case when installed in the cavity. Current is supplied to the electrical circuitry by typical electrical prong terminals projecting from a rear wall of the housing so that the prong terminals can be directly plugged into a conventional household electrical outlet.

25 Claims, 2 Drawing Sheets

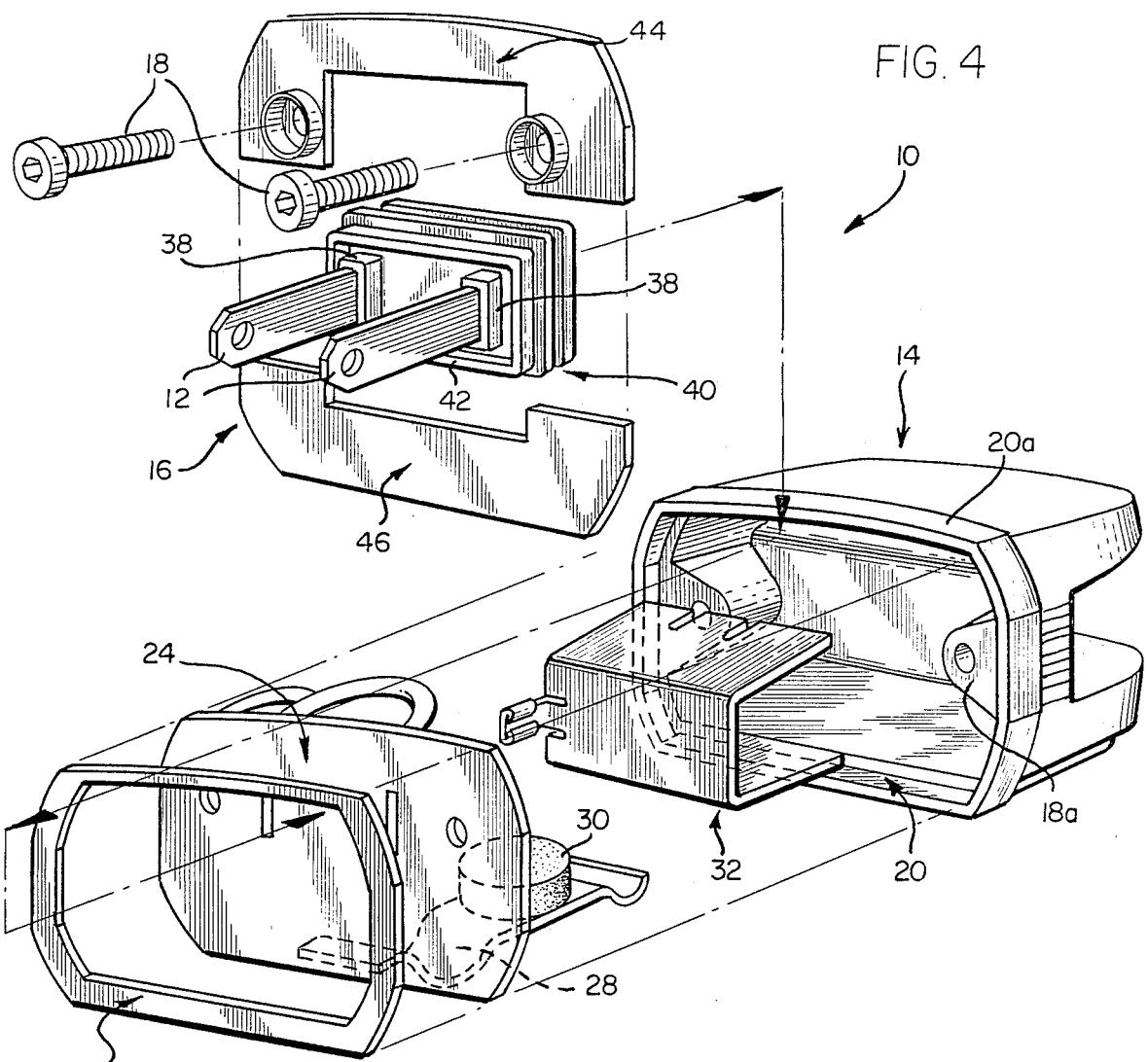
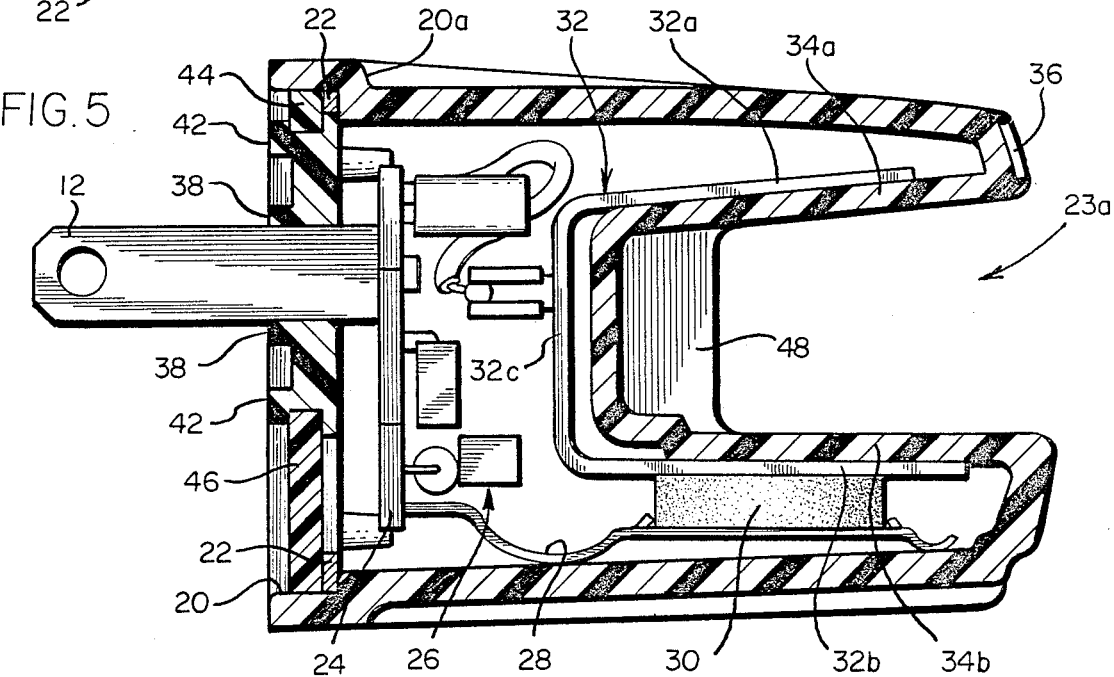

WALL PLUG LENS DISINFECTOR

BACKGROUND OF THE INVENTION

This invention relates to heat disinfecting appliances for contact lenses and similar small objects, and more particularly relates to such appliances which are plugged directly into an electrical wall outlet.

As described for example in U.S. Pat. No. 4,388,521, electrically heated disinfecting appliances for typical soft contact lenses have been developed in generally small units which can be directly plugged into household electrical wall outlets. The generally compact size of these disinfectors allows them to be self-supporting when plugged into the outlet which promotes convenience in regularly disinfecting the contact lenses. Also after disinfection the units may serve as a carrying case for the lenses. Since the lenses are disinfected in the appliance by electrically heating saline solution in which the lenses are submerged, spillage of the electrolytic saline solution in the vicinity of the electrical components can be a shock and fire hazard, particularly when salt and water accumulate immediately adjacent the electrical terminal prongs of the appliance. Such hazards are particularly acute when the cavities for submerging the lenses in saline solution are accessible to refilling with the solution while the appliance is electrically connected into the wall outlet. These hazards are eliminated by disinfecting appliances in accordance with this invention. Additionally, the appliances in accordance with this invention accommodate insertion of conventional removable side-by-side lens storage cases into the appliance for the lens disinfection.

SUMMARY OF THE INVENTION

In accordance with this invention, an appliance for electrically heated disinfection of contact lenses or similar objects is provided with a molded plastic housing having a recessed cavity for reception of a conventional side-by-side horizontal lens storage case containing the lenses immersed in disinfecting liquid, typically saline solution. The cavity has horizontally aligned opposite end openings through the sides of the housing and the openings are located and dimensioned to allow unobstructed sliding passage of the lens case from the cavity so that the lens case will fall by gravitation from the cavity through one of the openings when the housing is positioned other than horizontally, that is, rotated 90° to the horizontal to vertically align the openings. The cavity openings thus ensure that the lens case cannot be heated in the appliance in a vertical orientation which could result in damage to the lenses by virtue of the fact that the lenses are not properly submerged in the saline solution and can then be heated above the desired level of the disinfecting liquid. The housing further includes a floor wall below the cavity and a cover portion overlying the cavity which prevents access to the lens case and filling of the case with saline solution when installed in the cavity. Thus, it is not possible to fill the lens case when in the recess and the unit is plugged in. To effect filling, a user must remove the lens case from the unit, thus lessening the danger from spillage of the saline solution. The appliance further includes components for electrically heating the lens case when installed in the cavity.

In a preferred embodiment the cavity also includes a front opening through the housing which is contiguous with the end openings of the cavity through the sides of the housing so that the cavity resembles a front opening slot in the housing. The floor wall and cover portion of the housing which define the cavity are heated by engaging panels of a heat sink contained within the housing with heat generating electrical circuitry. Current is supplied to the electrical circuitry by typical electrical prong terminals projecting from a rear wall of the housing so that the prong terminals can be directly plugged into a conventional household electrical outlet.

The prong terminals are protected from accumulation of fluid which could cause a short circuiting bridge by providing insulating sleeves for each of the prongs which project from the rear wall. In addition a pair of projecting collars or rims surrounds both of the sleeves to further promote diversion of any fluid away from the prongs, for example if spillage should occur in the area of the plugged in unit. The rear wall is removable from the housing and the electrical prongs can be insert molded into the rear wall. In an alternative fabrication, the rear wall can be assembled from separately molded portions and the electrical prongs are insert molded in a central portion comprising the protective collar and sleeves. The housing has an out-turned lip adjacent the rear opening closed by the rear wall which defines one of the aforementioned rims or collars so that cleaning fluid is diverted away from the opening and the electrical circuitry contained within the housing.

BRIEF DESCRIPTION OF THE DRAWING

FIG. 4 is an exploded perspective view of the disinfecting appliance of FIGS. 1 and 2; and FIG. 5 is a sectional view taken along line 4—4 in FIG. 1, viewed in the indicated direction.

DESCRIPTION OF THE ILLUSTRATED EMBODIMENT

Figure 1:
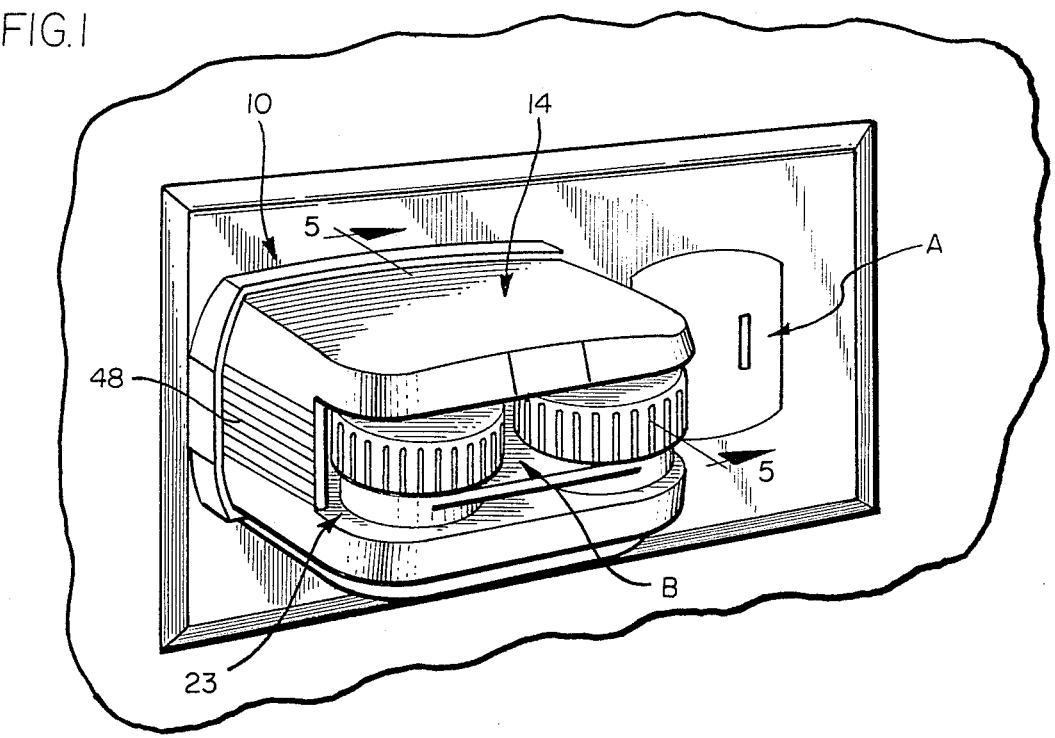
FIG. 1 is a perspective view of an electrically heated, lens disinfecting appliance in accordance with the subject invention, for heating a removable, conventional side-by-side contact lens storage case.
Figure 3:
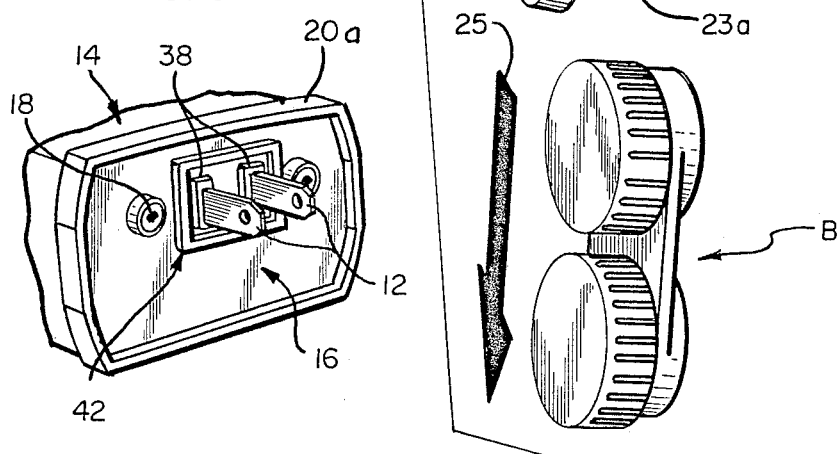
FIG. 3 is a fragmentary perspective view of the rear end of the appliance shown in FIGS. 1 and 2.

Referring now to FIGS. 1 and 4, an electrically heated disinfecting appliance, generally designated by reference character 10, is provided with a pair of rearwardly projecting prong terminals 12 for plugging the appliance 10 directly into a conventional electrical wall outlet A. The appliance 10 has a plastic housing including an integrally molded hollow shell portion 14 which has a rear opening closed by a removable rear wall assembly 16 carrying the projecting terminal prongs 12. The rear wall assembly 16 is mounted to close the rear opening of the shell 14 using screws 18 received in threaded bosses 18a integrally formed within the shell 14 or similarly suitable fasteners. As best shown in FIGS. 3-5, the wall assembly 16 fits within a surrounding ledge 20 on the rear of shell 14 and a gasket 22 or similarly provided sealant, is preferably clamped between the rear wall assembly 16 and the ledge 20 to ensure that saline solution or other fluids cannot leak within the shell 14 which houses electrical and heating components described hereinafter.

In order to prevent liquid during cleaning, or filling of the case from reaching the rear portion of the appliance 10, the shell 14 is not only integrally molded, but also provided with an outwardly raised flange or lip 20a which exteriorly surrounds the rear opening and ledge 20 so that moisture on the exterior of the shell 14 is effectively diverted away from the prongs 12 and away from entry into the rear opening and any contact with the electrical components within the shell. The terminal prongs 12 are themselves further protected by sleeves 38 and a collar 42 as more fully described hereinafter.

Figure 2:
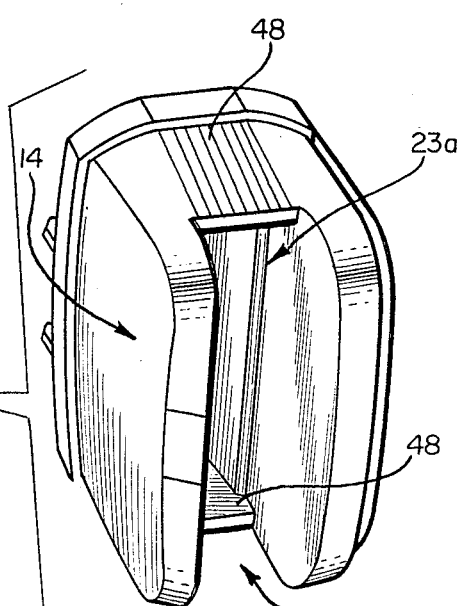
FIG. 2 is a perspective view of the disinfecting appliance of FIG. 1 shown in a rotated orientation from which the lens case has downwardly fallen by gravitation.

The front of the shell 14 has a recessed opening or cavity 23 Which is dimensioned to receive insertion of a conventional side-by-side dual contact lens storage case B in the normal horizontal orientation which promotes proper immersion of the contained lenses in the saline solution. As best shown in FIG. 2, the cavity 23 has both a front opening and two side openings 23a which preferably are unobstructed to ensure that if the appliance is not properly positioned, viz., rotated 90° to vertically align the side openings, the lens case B cannot be heated in the appliance and will fall by gravitation from the cavity as indicated by the arrow 25. The reason for ensuring that the lenses cannot be heated in vertical orientation of the side-by-side orientation of the case B is to ensure that the lenses are properly immersed in the saline so that the proper desired heating occurs without overheating the lenses. Since the receptacle pattern of most household electrical outlets provides for accepting terminal prongs in horizontal alignment as provided in the operating orientation of the appliance shown in FIG. 3, a less common outlet requiring vertically aligned prongs would also require use of an adaptor (not shown, but easily provided) to allow heating the appliance and lens case in the proper horizontal orientation ensured by the side openings 23a.

Referring now to FIGS. 4 and 5, the basic construction of the unit 10 is shown. In this regard, an electrical timer panel 24 is mounted in electrical contact with the inwardly projecting portion of the terminal prongs 12. The timer panel 24 supports timing circuitry 26 which controls the flow of current through a large leaf spring like contact 28 which supplies current to a suitable heating device 30. The heating device 30 is preferably a thermistor of the type in which the variable electrical resistance produces a maximum temperature. As more fully described in the aforementioned U.S. Pat. No. 4,388,521, the electrical circuitry 26 and thermistor 30 conduct heat to a heat sink generally designated 32 which similarly reaches the maximum temperature of the thermistor 30, for example approximately 80° C. The thermistor 30 is self-regulating and will maintain the 80° C. temperature. Timing of the heat cycle is controlled by conventional timing components in the circuit 26. The heat sink 32 is a generally C-profiled sheet of high thermally conductive metal with horizontally parallel leg panels 32a and 32b joined by a rear bight panel 32c. As best shown in FIG. 5, the upper and lower heat sink panels 32a, 32b, conform to and engage upper and lower inturned shell walls 34a, 34b, which define the recessed cavity 23 with openings at the front and sides of the shell 14. The upper and lower heat sink panels 32a, 32b, not only conduct heat to the shell walls 34a, 34b, which in turn conduct the disinfecting heat to the side-by-side lens case B as shown in FIG. 1, but in addition the heat sink panels 32a, 32b generate radiant heat which contribute to infrared heating of the lens case which is particularly effective in heating the top of a short lens case which may not be fully engaged against the upper shell wall 34a. Since the bottom of the lens case B is seated on the lower shell wall 34b the entire lens case is heated from below by conduction. Because the shell 14 will be heated during the disinfection cycle, a thermally sensitive indicator 36 or suitable alternative such as lighting will provide warning for care and handling the heated lens case B as well as the entire appliance 10.

The recessed cavity 23 and overhanging shell portion including upper wall 34a prevent filling of the fluid compartments of the lens case B with the electrically conductive saline solution while the lens case B is installed in the appliance, and thus ensures that the lens case B will be removed from the appliance 10 for such handling and occasional spillage of saline or cleaning solution away from appliance 10; this also eliminates any buildup of hazardous salt on any part of the housing, particularly adjacent the terminal prongs 18.

The unit 10 of the invention was also designed to prevent short circuiting of the prongs 10 when plugged in, from spillage which might occur in a bathroom or wash basin area. More specifically, the terminal prongs 12 are themselves protected against a short circuiting bridge and potentially resulting fire hazard by providing each of the prongs with a short molded insulating sleeve 38 which projects from the central portion 40 of the wall assembly 16. The sleeves 30 insure or promote any welling of water upon the sleeves 38 will be out of contact with the prongs 12. Additionally, a first collar or rim 42 similarly projects from wall portion 40 and circumscribes both of the sleeves 38 to further promote diversion of any fluid away from the prongs 12. Preferably, the prongs 12 are insert molded into the wall portion 40 so that the sleeves 38 and collar 42 are integrally molded with the central wall portion 40. In order to reduce the size of the insert molded piece, the central wall portion 40 is separately molded and then joined to upper and lower rear wall portions 44 and 46 such as by bonded tongue and mortise joints, as best shown in FIG. 5, to complete the rear wall assembly 16. Finally, the wall assembly 16 is recessed within shell 14 and is seated on the ledge 20. The rear edge of the shell 14 is raised to define a second collar or rim 20a which surrounds the collar 42 as well as the shielded prongs 12. This second rim 20a also serves to divert any water spilled upon the nit 10 away from the rear area and prongs 12.

Referring again to FIGS. 1 and 2, the side walls 48 of the shell 14 are surface-corrugated in order to improve the manual gripping of the appliance 10 particularly when plugging and unplugging the appliance into the electrical outlet A.

In light of the foregoing description of the embodied disinfector of the invention, it will be evident to those skilled in design of such appliances that various aspects may be modified without departing from the invention. As such, the scope of the invention is not limited by the particular embodiment illustrated and described herein and is defined by the appended claims and equivalents thereof.

The invention is claimed as follows:

1. An appliance for electrically heated disinfection of contact lenses or similar objects, by direct electrical connection of the appliance to an electrical wall outlet, comprising:

(A) a housing having a pair of opposite side walls and a receiving cavity for insertion of a storage compartment containing a lens and disinfecting liquid;

(B) said housing including a floor wall below said cavity and a cover portion overlying said cavity for preventing vertical access to said storage compartment when said compartment is installed in said cavity;

(C) said housing further including a pair of horizontally aligned side openings through said respective opposite housing side walls, each of said openings being located and dimensioned to allow sliding passage of said storage compartment therethrough so that the storage compartment will fall by gravitation from said housing cavity through one of said side openings when said housing is rotated 90° to vertically align said side openings; and (D) heating means for electrically generated heating of said storage compartment installed in said cavity, wherein said heating means comprises heat radiation means located above and separated from said cavity by a section of said cover portion, so that said radiation means generates downwardly directed radiant energy for heating said contact lens compartment without requiring heat conducting contact therewith.

2. The appliance according to claim 1 wherein said housing further includes a front opening into said receiving cavity, said front opening being located between said side openings and dimensioned for insertion of said storage compartment therethrough into said cavity.

3. The appliance according to claim 2 wherein said front opening is contiguous with both of said side openings.

4. An appliance for electrically heated disinfection of contact lenses or similar objects, by direct electrical connection of the appliance to an electrical wall outlet, comprising:

(A) a housing having a pair of opposite side walls and a receiving cavity for insertion of a storage compartment containing a lens and disinfecting liquid;

(B) said housing including a floor wall below said cavity and a cover portion overlying said cavity for preventing vertical access to said storage compartment when said compartment is installed in said cavity;

(C) said housing further including a pair of horizontally aligned side openings through said respective opposite housing side walls, each of said side openings being located and dimensioned to allow sliding passage of said storage compartment therethrough so that the storage compartment will fall by gravitation from said housing cavity through one of said side openings when said housing is rotated 90° to vertically align said side openings;

(D) said housing further including a rear wall having a pair of electrical prong terminals projecting therefrom for engagement in a conventional outlet socket, said rear wall further including a pair of insulating sleeves projecting therefrom, each said sleeve extending partially along a respective one of said prongs so that said sleeve surrounds and insulates the portion of said prong continuous with the exterior of said rear wall in order to deter any fluid contact with said prong, and (E) heating means for electrically generated heating of said storage compartment installed in said cavity.

5. The appliance according to claim 4 wherein said rear wall further includes a collar projecting therefrom and circumscribing both of said prongs and said sleeves in order to promote diversion of fluid away from said prongs.

6. The appliance according to claim 5 wherein said prongs are insert molded within said sleeves.

7. The appliance according to claim 4 wherein said prongs are insert molded with a portion of said rear wall comprising said collar, separate from at least a second molded portion of said rear wall to which said collar portion is joined in assembling said rear wall.

8. An appliance for electrically heated disinfection of contact lenses or similar objects by direct electrical connection of the appliance to an electrical wall outlet, comprising:

(A) a plastic housing including an integrally molded hollow shell portion having a rear opening closed by a removable rear wall, said shell having a receiving cavity for insertion of a storage compartment containing a lens and disinfectant liquid; wherein said housing further includes an outwardly extending lip projecting from one of said shell and rear wall adjacently surrounding said rear opening in order to divert any exterior moisture away from entry into said opening and shell;

(B) said shell including a floor wall below said cavity and a cover portion overlying said cavity for preventing vertical access to said storage compartment when said compartment is installed in said cavity;

(C) said shell further including a pair of horizontally aligned side openings from said cavity, each of said side openings being located and dimensioned to allow sliding passage of said storage compartment therethrough so that the storage compartment will fall by gravitation from said cavity through one of said side openings when said shell is rotated 90° to vertically align said side openings; and (D) heating means for electrically generated heating of said storage compartment within said cavity.

9. An appliance for electrically heated disinfection of contact lenses or similar objects by direct electrical connection of the appliance to an electrical wall outlet, comprising:

(A) a plastic housing including an integrally molded hollow shell portion having a rear opening closed by a removable rear wall, said shell having a receiving cavity for insertion of a storage compartment containing a lens and disinfectant liquid;

(B) said shell including a floor wall below said cavity and a cover portion overlying said cavity for preventing vertical access to said storage compartment when said compartment is installed in said cavity;

(C) said shell further including a pair of horizontally aligned side openings from said cavity, each of said side openings being located and dimensioned to allow sliding passage of said storage compartment therethrough so that the storage compartment will fall by gravitation from said cavity through one of said side openings when said shell is rotated 90° to vertically align said side openings;

(D) heating means for electrically generated heating of said storage compartment within said cavity.

(E) a pair of electrical prong terminals projecting from said rear wall for engagement in a conventional outlet socket or the like, wherein said electrical prongs are insert molded within a first portion of said rear wall to which a second portion of said rear wall is joined.

10. An appliance for electrically heated disinfection of contact lenses or similar objects, said appliance being adapted for direct electrical connection to an electrical wall outlet, or the like, said appliance, comprising: a molded housing, heating means disposed in said housing for electrically generating heat for the heat disinfection of contact lenses, said housing further including a rear wall having a pair of electrical prong terminals projecting therefrom for engagement in a conventional outlet socket or the like, said electrical prong terminals being in operative connection with said heating means, said rear wall further including a pair of insulating sleeves projecting therefrom, each said sleeve extending partially along a respective one of said prongs so that said sleeve surrounds and insulates the portion of said prong contiguous with the exterior of said rear wall in order to deter any fluid contact with said prong.

11. An appliance according to claim 10 wherein said housing includes a receiving cavity therein for insertion of a storage compartment containing a lens to be disinfected.

12. An appliance according to claim 10 wherein said rear wall further includes an outwardly extending lip projecting from said rear wall and adjacently surrounding said prong terminals in order to divert any exterior moisture away from said terminals.

13. An appliance according to claim 10 wherein said housing further includes an outwardly extending lip projecting in surrounding engagement with respect to said rear opening in order to divert exterior moisture away from the juncture of said shell portion and rear wall.

14. An appliance for electrically heated disinfection of contact lenses or similar objects, wherein said appliance is adapted for direct electrical connection to an electrical wall outlet or the like, said appliance comprising a molded plastic housing, heating means disposed within said housing for electrically generating heat for the heat disinfection of contact lenses, said housing further including a pair of electrical prong terminals projecting from said rear wall for engagement in a conventional outlet socket or the like, said rear wall further including an outwardly extending lip projecting from said rear wall and adjacently surrounding said prong terminals in order to divert any exterior moisture away from said terminals.

15. An appliance according to claim 14 wherein said housing further includes a receiving cavity for insertion of a storage compartment containing a lens to be disinfected.

16. An appliance according to claim 15 wherein said housing further includes a front opening into said receiving cavity from said front opening being located and dimensioned for insertion of said storage compartment therethrough into said receiving cavity.

17. An appliance according to claim 14 wherein said rear wall further includes a pair of insulating sleeves projecting therefrom, each said sleeve extending partially along a respective one of said prongs so that said sleeve surrounds and insulates the portion of said prong contiguous with the exterior of said rear wall in order to deter any fluid contact with said prong.

18. An appliance according to claim 17 wherein said housing further includes an outwardly extending lip projecting in surrounding engagement with respect to said rear opening in order to divert exterior moisture away form the juncture of said shell portion and said rear wall.

19. An appliance according to claim 14 wherein said housing further includes an outwardly extending lip projecting in surrounding engagement with respect to said rear opening in order to divert exterior moisture away from a juncture of said shell portion and rear wall.

20. An appliance for electrically heated disinfection of contact lenses or the like, said appliance being adapted for direct electrical connection to an electrical wall outlet or the like, said appliance comprising a molded plastic housing including a hollow shell portion having a rear opening, a rear wall member closing said opening; heating means disposed within said housing for generating heat for the heat disinfection of contact lenses, said housing including an outwardly extending lip projecting in surrounding engagement with respect to said rear opening in order to divert exterior moisture away from the juncture of said shell portion and rear wall.

21. An appliance according to claim 20 wherein said housing further includes a receiving cavity for insertion of a storage compartment containing a lens to be disinfected.

22. An appliance according to claim 21 wherein said housing further includes a front opening into said receiving cavity from said front opening being located and dimensioned for insertion of said storage compartment therethrough into said cavity.

23. An appliance according to claim 20 wherein said rear wall further includes a pair of insulating sleeves projecting therefrom, each said sleeve extending partially along a respective one of said prongs so that said sleeve surrounds and insulates the portion of said prong contiguous with the exterior of said rear wall in order to deter my fluid contact with said prong.

24. An appliance according to claim 23 wherein said rear wall further includes an outwardly extending lip projecting from said rear wall and adjacently surrounding said prong terminals in order to divert any exterior moisture away from said terminals.

25. An appliance according to claim 20 wherein said rear wall further includes an outwardly extending lip projecting from said rear wall and adjacently surrounding said prong terminals in order to divert any exterior moisture away from said terminal.

* * * * *